(12) United States Patent
Bunn

(10) Patent No.: US 12,318,249 B2
(45) Date of Patent: *Jun. 3, 2025

(54) PREMATURE BIRTH PREDICTION

(71) Applicant: Ultrasound AI, Inc., Highlands Ranch, CO (US)

(72) Inventor: Robert S Bunn, Highlands Ranch, CO (US)

(73) Assignee: Ultrasound AI Inc., Greenwood Village, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/586,358

(22) Filed: Feb. 23, 2024

(65) Prior Publication Data
US 2024/0315664 A1     Sep. 26, 2024

Related U.S. Application Data

(63) Continuation of application No. 17/573,246, filed on Jan. 11, 2022, now Pat. No. 11,969,289, which is a
(Continued)

(51) Int. Cl.
*A61B 8/00* (2006.01)
*A61B 8/06* (2006.01)
(Continued)

(52) U.S. Cl.
CPC .......... *A61B 8/0866* (2013.01); *A61B 8/06* (2013.01); *A61B 8/0875* (2013.01);
(Continued)

(58) Field of Classification Search
CPC ....... A61B 8/06; A61B 8/0866; A61B 8/0883; A61B 8/467; A61B 8/488; A61B 8/0875;
(Continued)

(56) References Cited

U.S. PATENT DOCUMENTS

| 8,828,981 B2 | 9/2014 | Creasy et al. |
| 10,650,929 B1 | 5/2020 | Beck et al. |

(Continued)

FOREIGN PATENT DOCUMENTS

| IN | 201941040741 A | 4/2021 |
| JP | 2018-140172 A | 9/2018 |

(Continued)

OTHER PUBLICATIONS

Office Action Issued in related Chinese Patent Application No. 202180043378.8 issued Dec. 28, 2023, 27 pages.
(Continued)

*Primary Examiner* — Joel F Brutus
(74) *Attorney, Agent, or Firm* — David J. Thibodeau; VLP Law Group LLP

(57) ABSTRACT

Systems and methods of predicting future medical events are based on the processing of medical images. The prediction of premature birth and estimation of gestational age based on ultrasound images are presented as illustrative examples. The new abilities to estimate the probability of future medical events, before they otherwise could be predicted, provides new avenues for the development of preventative treatments.

25 Claims, 2 Drawing Sheets

Related U.S. Application Data continuation of application No. PCT/US2021/038164, filed on Jun. 20, 2021, and a continuation of application No. 17/352,290, filed on Jun. 19, 2021, now Pat. No. 11,266,376, said application No. PCT/US2021/038164 is a continuation of application No. 17/352,290, filed on Jun. 19, 2021, now Pat. No. 11,266,376.

(60) Provisional application No. 63/041,360, filed on Jun. 19, 2020.

(51) Int. Cl.

| A61B 8/08 | (2006.01) |
|---|---|
| G06T 7/00 | (2017.01) |
| G06T 7/20 | (2017.01) |
| G16H 10/60 | (2018.01) |
| G16H 30/20 | (2018.01) |
| G16H 30/40 | (2018.01) |
| G16H 50/20 | (2018.01) |

(52) U.S. Cl.
CPC ............ *A61B 8/0883* (2013.01); *A61B 8/467* (2013.01); *A61B 8/488* (2013.01); *G06T 7/0016* (2013.01); *G06T 7/20* (2013.01); *G16H 10/60* (2018.01); *G16H 30/20* (2018.01); *G16H 30/40* (2018.01); *G16H 50/20* (2018.01); *G06T 2207/10132* (2013.01); *G06T 2207/20081* (2013.01); *G06T 2207/30008* (2013.01); *G06T 2207/30044* (2013.01); *G06T 2207/30048* (2013.01); *G06T 2207/30104* (2013.01)

(58) Field of Classification Search
CPC . G06T 2207/10132; G06T 2207/20081; G06T 2207/30008; G06T 2207/30044
See application file for complete search history.

(56) References Cited

U.S. PATENT DOCUMENTS

| 2004/0236193 | A1 | 11/2004 | Sharf |
| 2006/0241510 | A1 | 10/2006 | Halperin et al. |
| 2009/0093717 | A1 | 4/2009 | Carneiro et al. |
| 2009/0169074 | A1 | 7/2009 | Avinash et al. |
| 2010/0312115 | A1 | 12/2010 | Dentinger |
| 2011/0248818 | A1 | 10/2011 | Hashim-Waris |
| 2012/0135427 | A1 | 5/2012 | Kypros et al. |
| 2014/0018678 | A1 | 1/2014 | Donnelly et al. |
| 2014/0089004 | A1 | 3/2014 | Frey et al. |
| 2015/0148657 | A1 | 5/2015 | Shashar et al. |
| 2015/0342560 | A1 | 12/2015 | Davey et al. |
| 2016/0071266 | A1 | 3/2016 | Srivastava et al. |
| 2016/0228505 | A1 | 8/2016 | Stossel et al. |
| 2017/0000683 | A1 | 1/2017 | Samec et al. |
| 2017/0086785 | A1 | 3/2017 | Bjaerum |
| 2017/0091402 | A1 | 3/2017 | Salafia et al. |
| 2017/0216335 | A1 | 8/2017 | Mangano |
| 2017/0357844 | A1 | 12/2017 | Comaniciu et al. |
| 2018/0032666 | A1 | 2/2018 | Sun et al. |
| 2018/0153504 | A1 | 6/2018 | Herickhoff et al. |
| 2019/0008674 | A1* | 1/2019 | Myers .................. A61F 6/08 |
| 2019/0021698 | A1 | 1/2019 | Raghvan et al. |
| 2019/0034590 | A1 | 1/2019 | Oren et al. |
| 2019/0154704 | A1 | 5/2019 | Davis et al. |
| 2019/0209116 | A1 | 7/2019 | Sjostrand et al. |
| 2019/0246904 | A1 | 8/2019 | Kim et al. |
| 2019/0251638 | A1 | 8/2019 | Braz et al. |
| 2019/0367987 | A1 | 12/2019 | Hamamah et al. |
| 2020/0005899 | A1 | 1/2020 | Nicula et al. |
| 2020/0005901 | A1 | 1/2020 | Cohen et al. |
| 2020/0022674 | A1 | 1/2020 | Egorov |
| 2020/0069292 | A1 | 3/2020 | Abolmaesumi et al. |
| 2020/0077947 | A1 | 3/2020 | Shi et al. |
| 2020/0147006 | A1 | 5/2020 | Charney et al. |
| 2020/0149110 | A1 | 5/2020 | Targan et al. |
| 2020/0168310 | A1 | 5/2020 | Westin et al. |
| 2020/0170614 | A1 | 6/2020 | Kim et al. |
| 2021/0068905 | A1 | 3/2021 | Quaid et al. |
| 2021/0090254 | A1 | 3/2021 | Gong et al. |
| 2021/0118559 | A1 | 4/2021 | Lefkofsky |
| 2021/0128115 | A1 | 5/2021 | Mapiye et al. |
| 2021/0217166 | A1 | 7/2021 | Graule et al. |
| 2021/0287513 | A1 | 9/2021 | Mazar et al. |
| 2021/0307702 | A1 | 10/2021 | Moon |
| 2022/0028551 | A1 | 1/2022 | Jordan et al. |
| 2022/0067922 | A1 | 3/2022 | Yu |
| 2022/0133260 | A1 | 5/2022 | Bunn |
| 2022/0164635 | A1 | 5/2022 | Johansen et al. |
| 2022/0192501 | A1 | 6/2022 | Shuler |
| 2022/0328189 | A1 | 10/2022 | Zhou et al. |
| 2022/0400963 | A1 | 12/2022 | Bucklet et al. |

FOREIGN PATENT DOCUMENTS

| KR | 10-2020-0013161 A | 2/2020 |
| WO | 2020/061590 A1 | 3/2020 |

OTHER PUBLICATIONS

PCT/US21/38164 International Search Report and Written Opinion, mailed Sep. 30, 2021.
PCT/US23/011845 International Search Report and Written Opinion, mailed Apr. 27, 2023.
PCT/US24/014349 International Search Report and Written Opinion, mailed May 7, 2024.
PCT/US24/019803 International Search Report and Written Opinion, mailed Jun. 17, 2024.
PCT/US24/014353 International Search Report and Written Opinion, mailed May 7, 2024.
PCT/US24/014356 International Search Report and Written Opinion, mailed May 9, 2024.
Kuo et al., "Automation of the kidney function prediction and classification through ultrasoundbased kidney imaging using deep learning." In: npj Digital Medicine vol. 2, Article No. 29 (2019), [online] [retrieved on Apr. 17, 2024 (Apr. 17, 2024)] Retrieved from the Internet < URL: https://www.nature.com/articles/s41746-019-0104-2#ethIcs>.
CN 202180043378.8, Response to first office action issued Dec. 28, 2023, dated May 10, 2024.
CN 202180043378.8, Rejection Decision issued May 18, 2024.
CN 202180043378.8, Response to Rejection Decision iissued May 18, 2024, dated Aug. 19, 2024.
EP 21825348.2 EESR Issued Jun. 18, 2024.
Oelze et al., "Review of Quantitative Ultrasound: Envelope Statistics and Backscatter Coefficient Imaging and Contributions to Diagnostic Ultrasound", IEEE Transactions on Ultrasonics, Ferroelectrics, and Frequency Control, IEEE, USA, vol. 63, No. 2, Feb. 1, 2016 (Feb. 1, 2016), pp. 336-351, XP011597293, ISSN: 0885-3010, DOI: 10.1109/TUFFC.2015.2513958 [retrieved on Jan. 29, 2016].
Suff Natalie et al: "The prediction of preterm delivery: What is new?", Seminars in Fetal and Neonatal Medicine, Elsevier, GB, vol. 24, No. 1, Sep. 28, 2018 (Sep. 28, 2018), pp. 27-32, XP085591331, ISSN: 1744-165X, DOI: 10.1016/J.SINY.2018.09.006.
Pizzella Stephanie et al: "Evolving cervical imaging technologies to predict preterm birth", Seminars in Immunopathology, Springer Berlin Heidelberg, Berlin/Heidelberg, vol. 42, No. 4, Jun. 10, 2020 (Jun. 10, 2020), pp. 385-396, XP037251810, ISSN: 1863-2297, DOI: 10.1007/S00281-020-00800-5 [retrieved on Jun. 10, 2020].
European Application No. EP 21825348.2, Response to EESR issued Jul. 5, 2024, filed Dec. 30, 2024.
Japanese Application No. JP 2022-574786, Response to Notice of Reasons for Refusal issued Sep. 3, 2024, filed Nov. 19, 2024.
Korean Application No. KR 10-2023-7000075; Response to Office Action issued Oct. 21, 2024, filed Dec. 23, 2024.

(56) References Cited

OTHER PUBLICATIONS

Japanese Application No. JP 2022-574786—Notice of Reasons for Refusal issued Feb. 4, 2025.
JP 2022-574786, Notice of Reasons for Refusal, Issued Sep. 3, 2024.
KR 10-2023-7000075, Office Action, Issued Oct. 21, 2024.

* cited by examiner

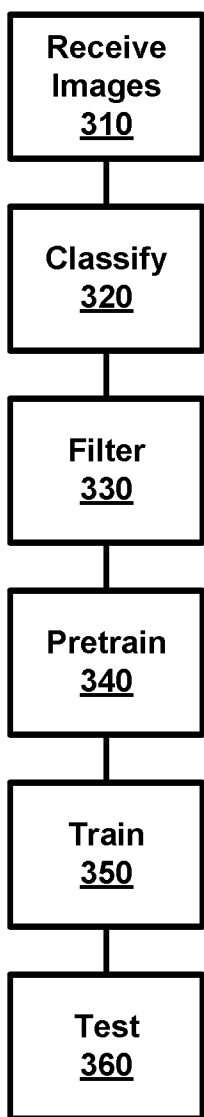
FIG. 3
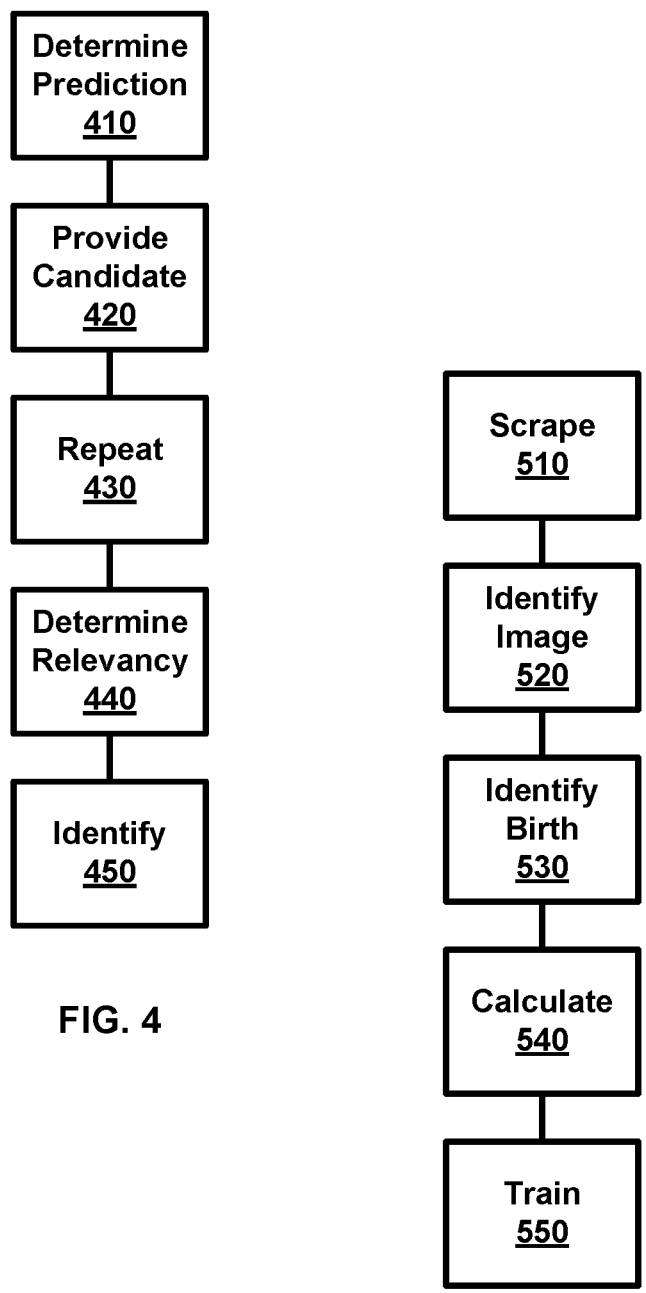
FIG. 4
FIG. 5

PREMATURE BIRTH PREDICTION

CROSS-REFERENCE TO RELATED APPLICATIONS

This application is a continuation of U.S. non-provisional application Ser. No. 17/573,246 filed Jan. 11, 2022 which is a continuation of U.S. non-provisional application Ser. No. 17/352,290 filed Jun. 19, 2021, now U.S. Pat. No. 11,266,376, which claims benefit and priority to U.S. provisional patent application No. 63/041,360 filed Jun. 19, 2020; U.S. non-provisional application Ser. No. 17/573,246 is also a continuation of International Application PCT/US21/38164 filed Jun. 20, 2021 which claims benefit and priority to both U.S. patent application Ser. No. 17/352,290 and U.S. provisional patent application No. 63/041,360. The disclosures of all of the above-mentioned applications are incorporated herein by reference in their entireties.

BACKGROUND

Field of the Invention

The invention is in the field of predictive diagnostics applied to a wide range of medical conditions including but not limited to pregnancy.

Related Art

A premature birth is a birth that takes place more than three weeks before the baby's estimated due date. In other words, a premature birth is one that occurs before the start of the 37th week of pregnancy. Premature babies, especially those born very early, often have complicated medical problems. Typically, complications of prematurity vary. But the earlier the baby is born, the higher the risk of complications.

A fetal ultrasound (sonogram) is an imaging technique that uses sound waves to produce images of a fetus in the uterus. Fetal ultrasound images can help a health care provider evaluate a baby's growth and development and monitor a pregnancy. In some cases, fetal ultrasound is used to evaluate possible problems present at the time of the ultrasound or to help confirm a diagnosis. The first fetal ultrasound is usually done during the first trimester to confirm the pregnancy and estimate gestational age. The next ultrasound is typically offered during the second trimester, when anatomic details are visible.

SUMMARY

Ultrasound, and optionally other medical imaging techniques, are used to generate predictions regarding the outcome of medical condition such as pregnancy. These predictions can include, among other things, an estimated date of birth, premature birth, and/or a need to induce birth. The predictions are optionally used to provide specific corrective treatment in anticipation of a premature birth. The predictions provide hitherto unavailable methods of treatment in which anticipatory treatments are provided to prevent or otherwise alleviate undesirable outcomes. Systems and methods of the invention include prediction, anticipatory treatments, and/or development of treatments based on predictions.

Various embodiments include using medical images, e.g., ultrasound images, as an input to a machine learning system configured to produce a quantitative predictive output based on the images. These machine learning systems may use regression, a classification approach, and/or other machine learning algorithms. For example, any regression algorithm that outputs ranges may be used, e.g., quantile regression. In some embodiments, multiple algorithms are combined in a single AI in a unique approach.

Various embodiments also include preprocessing of images and/or pretraining of machine learning systems. For example, preprocessing of images has been found to be useful where medical images are of poor or variable quality or of variable size, e.g., where the images are ultrasound images.

Various embodiments include real-time feedback during image acquisition. This feedback may be directed at image selection, obtaining better images, and/or obtaining more useful images. The feedback may be based on processing of images already obtained. For example, in some embodiments, the evaluation of initial images is used to guide the further acquisition of images having predictive and/or diagnostic value. Optionally, image processing systems are included in an image capture device or are connected to an image processing device using a communication network such as a local area network or the Internet.

Various embodiments of the invention comprise a medical prediction system configured to predict premature births, the system comprising: an image storage configured to store ultrasound images, the ultrasound images including, for example, a fetus; image analysis logic configured to provide an estimate that a fetus will be born prematurely based on the ultrasound images; a user interface configured to provide at least the estimate that the fetus will be born prematurely to a user; and a microprocessor configured to execute at least a part of the image analysis logic. The image analysis logic optionally comprises: first logic configured to estimate a gestational age of the fetus based on the ultrasound images, the gestational age being at a time the ultrasound images were generated, second logic configured to estimate a time until birth of the fetus based on the ultrasound images, and logic configured to calculate an estimated gestational age of the fetus at birth of the fetus. Days until delivery can be calculated directly without the gestational age, in which case a medical provider can calculate how many days early the birth would be.

Various embodiments of the invention include a method of generating a quantitative prediction of premature birth, the method comprising: obtaining a set of medical images including a fetus; analyzing the medical images using a machine learning system to produce the quantitative prediction, the quantitative prediction including an estimate of time until birth of the fetus or an estimate of a gestational age of the fetus at birth; and providing the quantitative prediction to a user.

Various embodiments of the invention include method of training a medical prediction system, the method comprising: receiving a plurality of medical images, the medical images optionally including ultrasound images of a fetus during pregnancy; optionally filtering the images; optionally classifying the images according to the views or features included within the images; optionally pretraining a neural network to recognize features within the images or types of images; training the neural network to provide a quantitative prediction regarding birth of the fetus, the quantitative prediction including an estimate of a gestational age of the fetus at birth, or including an estimate of a current gestational age of the fetus and an estimate of remaining time until birth of the fetus; and optionally testing the trained neural network, to determine accuracy of the quantitative predictions.

Various embodiments of the invention include a method of acquiring ultrasound images for training a neural network, the method comprising: scraping a social media account; identifying a fetal ultrasound image in the social media account; identifying a birth announcement within the social media account; calculating a time between posting of the ultrasound image on the social media account and posting of the birth announcement on the social media account; and using the ultrasound image and calculated time to train a neural network to generate a prediction that an ultrasound image is indicative of a premature birth, the prediction optionally being a quantitative prediction.

Various embodiments of the invention include a method of identifying a beneficial therapy based on medical predictions, the method comprising: determining a quantitative prediction of a future medical condition, the quantitative prediction including a probability that the medical condition will occur within a future time range and being based on analysis of medical images of a patient; providing a candidate therapy for the medical condition to the patient; repeating the steps of determining a quantitative prediction of a future medical condition and providing a candidate therapy for plurality of patients; determining if the candidate therapy resulted in a statistically relevant benefit to the plurality of patients at their respective time ranges; and identifying the candidate therapy as the beneficial therapy based on the statistically relevant benefit.

BRIEF DESCRIPTION OF THE DRAWINGS

FIG. 3 illustrates methods of training a medical prediction system, according to various embodiments of the invention.

FIG. 4 illustrates methods of identifying a beneficial therapy based on medical predictions, according to various embodiments of the invention.

FIG. 5 illustrates methods of acquiring ultrasound images, according to various embodiments of the invention.

DETAILED DESCRIPTION

While artificial intelligence systems, such as machine learning systems and expert systems, have been used to identify features in medical images, e.g., read chest x-rays, there have been limited advances in the field of medical prediction using medical images. In contrast to prior diagnostic uses of artificial intelligence, the systems and methods disclosed herein demonstrate the predictive value of processing medical images, and optionally other data, using artificial intelligence. As an illustrative example, the predictive value of such processing is described relative to the prediction of premature birth using ultrasound.

The systems and methods disclosed herein are capable of providing a quantitative prediction that a fetus will be born early (e.g., preterm), or a quantitative prediction of some other medical event. The quantitative nature of these predictions is in sharp contrast with the prior art. For example, a quantitative prediction is more than merely identification of a pregnancy as being "at risk." As used herein, a "quantitative prediction" includes at least one of: a probability, a classification within more than one premature class, or a time estimate. In the case of a premature birth prediction, the time estimate may be represented by an estimated number of days to birth and/or an estimated gestational age at birth. These estimates may be represented by two, three or more time ranges. The benefit of a quantitative prediction is that it provides much more actionable information in comparison to a mere (and error prone) "at risk" classification.

Figure 1:
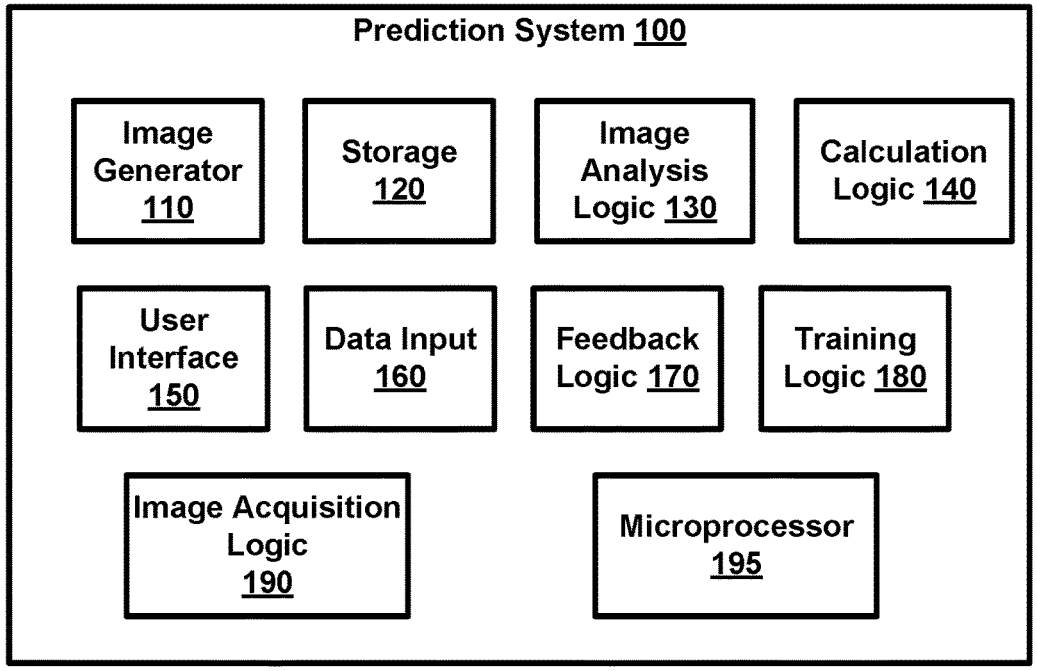
FIG. 1 illustrates medical prediction systems configured to predict medical outcomes, according to various embodiments of the invention.

FIG. 1 illustrates a medical Prediction System 100 configured to predict medical outcomes, according to various embodiments of the invention. Prediction System 100 may include multiple devices, such as an ultrasound system and a computing device configure for image processing. Prediction System 100 is optionally configured to communication between various components and/or external devices via a communications network, such as the Internet.

Image processing to generate predictions include generation of an estimate that a specific medical condition and/or event will occur in the future, e.g., during a time period starting at a future date. The estimate is optionally represented as an absolute or relative probability. Further, the estimate may include a temporal component. For example, an estimate may be that there is a 66% likelihood of a premature birth, that a birth between 33-34 weeks of gestation is more likely than a birth between 37-38 weeks of gestation, and/or that a birth has a 50% probability of occurring by 34 weeks of gestation. In another example, a prediction may include a probability that lung or breast cancer will occur within a future period of time.

Prediction System 100 includes an optional Image Generator 110 configured to generate images. Image Generator 110 may include a prior art ultrasound, or other imaging, system that is further configured to provide images to other elements of Prediction System 100 for processing, e.g., via a computer network. In various embodiments Image Generator 110 is a system including an image generation device and any combination of one or more of the elements of Prediction System 100. For example, Image Generator 110 may be an ultrasound device that includes Storage 120, Image analysis Logic 130, User Interface 150 and Feedback Logic 170 (as discussed further elsewhere herein). In various embodiments, Image Generator 110 includes imaging devices based on radiograph (e.g., x-rays), magnetic resonance imaging devices, nuclear imaging devices, ultrasound imaging systems, elastography devices, photoacoustic devices, tomography devices, echocardiography devices, magnetic particle imaging systems, spectroscopic (e.g., near-infrared) devices, and/or the like.

In some embodiments, other elements of Prediction System 100 are directly connected to or included within Image Generator 110. For example, Image Generator 110 may include an ultrasound machine having Image Analysis Logic 130 configured for providing real-time feedback via Feedback Logic 170 to guide the acquisition of ultrasound data and/or images. In some embodiments, Image Generator 110 comprises a sound source, a sound detector and logic configured to generate the ultrasound images based on sound detected by the sound detector. Optionally, Image Generator 110 is configured to adapt the generation of ultrasound images based on feedback from Image Analysis Logic 130. For example, the sound generation, focus and processing may be adapted to better detect blood perfusion in small capillaries of a fetus, in response to an indication from Image Analysis Logic 130 that images including such information would provide better predictions and estimates.

Image Generator 110 is optional in embodiments wherein externally obtained images are received by Prediction System 110 or where raw imaging data is used for prediction. For example, Image Generator 110 is optional in embodiments were raw ultrasound (sonogram) data rather than images are processed to generate medical predictions. In some embodiments, images and/or raw data is received by Prediction System 100 via a communication network such as the Internet. The images generated by Image Generator 110 can include a sequence of images representative of motion of a fetus. For example, a sequence may show blood flow, capillary profusion, heartbeat, and/or the like. Such a sequence may also include Doppler information related to direction and velocity of movement.

Prediction System 100 further comprises a Storage 120. Storage 120 includes digital memory configured to store: raw sensor data, medical images, medical data, executable code (logic), neural networks, and/or the like. For example, Storage 120 may be configured to store raw sensor data generated by a photon or acoustic detector, which could be used to generate x-ray or ultrasound images. As discussed elsewhere herein, Storage 120 optionally includes memory circuits and optionally includes data structures configured to manage and store any of the above data types. Ultrasound images stored in Storage 120, are optionally 600×600 pixels and random crops of 400×400 (or at least 300×300) are optionally used for the training and/or predictions discussed herein. The "ultrasound images" discussed herein optionally include three dimensional renderings based on ultrasound data.

In some embodiments, Storage 120 specifically includes circuits configured to store ultrasound images of a mother and/or fetus during pregnancy. The ultrasound images may be generated in one or more acquisition session. For example, a first set of ultrasound images may be obtained in a single sitting by a sonographer in a first session and a second set of ultrasound images may be obtained in a second session that occurs at least 1, 2, 5, 7, 15, 21, 30, 60, 90 or 180 days later, or any range between these values. The ultrasound images of a particular mother and/or fetus may be generated over a period of time including any of the above time durations. For example, in some cases a mother may undergo a weekly ultrasound in a high-risk pregnancy. The ultrasound images optionally include Doppler data and/or a sequence of images (e.g., video) representing motion of the fetus. For example, the ultrasound images may indicate fetal heart beats or blood flow. The ultrasound images may further include information regarding density of tissues, fluids or bone of the fetus. Images found to be useful for making preterm predictions include images showing: Fetal Heart Rate, the Umbilical Artery, the Uterus (including Lower Uterine Segment), the Cervix, a Cervical view taken specifically to measure the length of the cervix, an Amniotic Fluid Index view, the Abdominal Circumference (AC), the Biparietal diameter (BPD) along with all other views of the brain, Femur, Humerus, Endometrium (e.g., thickness and vascularization), the edge of the placenta relative to the cervix, the fetal kidneys, the placenta, the adnexa, and/or the like. In some embodiments, images useful for estimating the gestational age of the fetus are processed with images useful for estimating the gestational age of the placenta. Differences between these estimates are then used in predicting preterm births.

Prediction System 100 further includes Image Analysis Logic 130 configured to provide a quantitative prediction that a fetus will be born prematurely based on the ultrasound images and optionally clinical data. This prediction includes estimates that may take a wide variety of forms. For example, the prediction may be based on an estimate of a current gestational age of the fetus and an estimate of a (remaining) time before birth (time until delivery, or number of days earlier than the standard of 280 days). Or, the estimation may include a probability that the fetus will be born with indicators of premature birth (e.g., low birth weight), this estimate optionally being independent of current gestational age. Predictions made by Image Analysis Logic 130 can also include probability estimates that a doctor will chose to induce birth while still preterm or at term. For example, a prediction may include a probability that a doctor will choose to induce preterm birth because of a condition such as preeclampsia. Such prediction may be made at least 1, 2, 3 or 4 weeks or 1, 2, 3, 4, 5, 6 or 7 months before inducement occurs. In the case of preeclampsia, a caregiver may need to cause inducement immediately once the condition has presented itself in a life-threatening form whether the fetus is preterm or not.

In some embodiments, Image Analysis Logic 130 comprises first logic configured to estimate a gestational age of the fetus based on the ultrasound images, and second logic configured to estimate a time until birth of the fetus based on the ultrasound images. For example, the first logic may be configured to use ultrasound images to estimate the gestational age at a time the ultrasound images were generated, while the second logic is configured to estimate the remaining time until birth of the fetus. In these embodiments, further logic in Image Analysis Logic 130 is then configured to calculate an estimated gestational age of the fetus at birth by adding the estimated gestational age to the remaining time until birth. The first logic and the second logic are optionally disposed within a same machine learning system. For example, they may be included in a same neural network that receives the ultrasound images as inputs and that outputs both the gestational age and the remaining time. By calculating the estimated gestational age and the remaining time until birth using the same machine learning system, the errors in both these calculations may be related such that the overall error is less than would be expected if the two errors were independent.

Image Analysis Logic 130 may be configured to perform the above calculations using a wide range of machine learning algorithms. For example, in some embodiments Image Analysis Logic 130 is configured to use a regression algorithm (e.g., quantile regression) to provide an estimate that the fetus will be born prematurely, and optionally to estimate the time until birth. Quantile regression, and the like, predict a range the actual answer will likely fall into, rather than merely a single value answer. In various embodiments, any regression system that predicts a range or ranges as opposed to a point value may be used in Image Analysis Logic 130. Use of a range as an estimation prevents overfitting of the data and is useful when ultrasound images used for training may be mislabeled. Image Analysis logic is typically configured to make the predictions and estimates based on sets of ultrasound images, rather than analysis of a single ultrasound image.

In some embodiments, Image Analysis Logic 130 is configured to provide an estimate that the fetus will be born prematurely using a classification algorithm. In contrast to the traditional classification of births into two classes "normal" and "preterm" (where preterm is 22 or more days early), the classification algorithm optionally includes three, four or more classifications related to birth timing. A neural network using the classification algorithm can assign a pregnancy to a specific class, e.g., time range of estimated birth, thus making a quantitative prediction regarding the remaining time to birth. These classifications can include, for example, "preterm" at 29 or more days early, "borderline" at 14 to 28 days early and "normal" at less than 14 days early. In practice the date ranges for these classifications may be varied by +/−1-4 days in different implementations. In alternative embodiments, more and/or different classifications are used.

When classification algorithms are used a "label smoothing" function is optionally applied. A smoothing function may be beneficial because some training images may have incorrect labels due to a condition having not yet developed at a time ultrasound images are generated. This smoothing function can have, for example, the form described below, optionally wherein epsilon (ε) is 0.05, 0.1, 0.3 or greater.

Sample Label Smoothing

Instead of using one-hot encoded vector, a noise distribution u(y|x) is introduced. The new ground truth label for data $(x_i, y_i)$ becomes:

$$p'(y \mid x_i) = (1 - \varepsilon)p(y \mid x_i) + \varepsilon u(y \mid x_i)$$

$$= \begin{cases} 1 - \varepsilon + \varepsilon u(y \mid x_i) & \text{if } y = y_i \\ \varepsilon u(y \mid x_i) & \text{otherwise} \end{cases}$$

Where ε is a weight factor, $\varepsilon \in [0, 1]$, and note that $\Sigma_{y=1}^{K} p'(y|x_i) = 1$ This new ground truth label is used as a replacement for the one-hot encoded ground-truth label in a loss function.

$$L' = -\sum_{i=1}^{n}\sum_{y=1}^{K} p'(y \mid x_i) \log q_\theta(y \mid x_i)$$

$$= -\sum_{i=1}^{n}\sum_{y=1}^{K} [(1 - \varepsilon)p(y \mid x_i) + \varepsilon u(y \mid x_i)] \log q_\theta(y \mid x_i)$$

Or, $$L' = \sum_{i=1}^{n}\left\{(1-\varepsilon)\left[-\sum_{y=1}^{K} p(y \mid x_i) \log q_\theta(y \mid x_i)\right] + \varepsilon\left[-\sum_{y=1}^{K} u(y \mid x_i) \log q_\theta(y \mid x_i)\right]\right\}$$

$$= \sum_{i=1}^{n} [(1 - \varepsilon)H_i(p, q_\theta) + \varepsilon H_i(u, q_\theta)]$$

One can see that for each example in the training dataset, the loss contribution is a mixture of the cross entropy between the one-hot encoded distribution and the predicted distribution $H_i(p, q_\theta)$, and the cross entropy between the noise distribution and the predicted distribution $H_i(u, q_\theta)$. During training, if the model learns to predict the distribution confidently, $H_i(p, q_\theta)$ will go close to zero, but $H_i(u, q_\theta)$ will increase dramatically. Therefore, with label smoothing, one introduces a regularizer $H_i(u, q_\theta)$ to prevent the model from predicting too confidently.

In some embodiments, label smoothing is used when the loss function is cross entropy, and the model applies the softmax function to the penultimate layer's logit vectors z to compute its output probabilities p. Label smoothing is a regularization technique for classification problems to prevent the model from predicting the labels too confidently during training and generalizing poorly. See, for example, https://leimao.github.io/blog/Label-Smoothing/.

In some embodiments, both a regression algorithm and a classification algorithm are used to predict premature birth and/or time to birth. For example, Image Analysis Logic 130 can include two separate neural networks, one configured to apply the regression algorithm (that outputs a range) and the other configured to apply the classification algorithm. In this case, the classification algorithm may be applied before the regression algorithm and the regression algorithm is optionally applied separately to each class.

Alternatively, both the regression algorithm and the classification algorithm may be applied by the same neural network. In such embodiments, the neural network is trained to produce both a classification and a regression-based prediction, both of which are quantitative. A regression algorithm outputs one or more values for each percentile chosen. For example, some embodiments use 10%, 25%, 50%, 75%, 90% percentiles for outputs (which represent percentiles of a quantitative prediction), and each of these percentiles may be associated with a probability and/or a confidence measure. From a set of image inputs, the neural network of Image Analysis Logic 130 typically generates one or more value for each percentile chosen. Multiple outputs from distinct algorithms may be used to confirm a prediction of premature birth and/or time to birth. This scenario is optionally used to establish confidence in the overall prediction since the regression and classification algorithms should produce the same result.

Image Analysis Logic 130 may employ other machine learning algorithms or combinations thereof, in addition to or as an alternative to regression and classification. For example, Image Analysis Logic 130 may be configured to apply a regression that outputs an estimated range, a range being more accurate and/or useful than single point predictions. However, single point predictions can be used if many neural networks are generated (each trained on a different subset of the images/data) from different subsets of the data, which are then statistically analyzed to form an average and/or distribution. In some embodiments, a Bayesian convolutional neural network is used to capture the epistemic uncertainty, which is the uncertainty about the model fitness due to limited training data. Specifically, instead of learning specific weight (and bias) values in the neural network, the Bayesian approach learns weight distributions, from which it is sample to produce an output for a given input, to encode weight uncertainty. Bayesian networks can also be used in a similar fashion in the classification approaches to prediction discussed herein.

As noted elsewhere herein, Image Analysis Logic 130 may be configured (using the above algorithm/machine learning techniques) to provide an estimate that a fetus will be born prematurely. This estimate can include a probability of premature birth, a current estimated gestational age, an estimated time until birth of the fetus, and/or an estimated total gestation time. These estimates are based on the processing of ultrasound images, and optionally other factors associated with the pregnancy. For example, Image Analysis Logic 130 may be configured to generate the above estimates based on clinical data. This clinical data can include, for example, one, two, three or more of: mother genetics, mother weight, mother pregnancy history, mother blood glucose, mother heart function, mother kidney function, mother blood pressure, placenta condition, mother infections, mother nutrition, mother drug use (smoking & alcohol consumption), mother age, mother's socioeconomic status, mother's home environment, mother's income, mother's race, and/or mother cervix or uterus characteristics. Image Analysis Logic 130 is optionally configured to take any one or combination of these clinical data as inputs to make the estimates and predictions discussed herein based, in part, on these clinical data.

Prediction System 100 optionally further includes Calculation Logic 140 configured to calculate useful outputs based on estimates made by Image Analysis Logic 130. For example, Calculation Logic 140 may be configured to calculate a total gestation time based on a current gestation age and an estimated time to birth. Calculation Logic 140 may be configured to calculate a total gestation time based on a probability distribution (e.g., a distribution represented by percentiles). Calculation Logic 140 may be configured to calculate a probability of a preterm birth based on an estimated time to birth or estimated total gestation time. For example, Calculation Logic 140 may apply a distribution function to the estimates made by Image Analysis Logic 130 and produce a probability distribution therefrom. In some embodiments, Image Analysis Logic 130 is configured to generate characteristics of this distribution function. For example, in some embodiments, an estimate of the reliability of an expected time to birth and this estimate of reliability can be used to determine a width (e.g., standard deviation) of the distribution function. Calculation Logic 140 is optionally included in Image Analysis Logic 110.

Prediction System 100 optionally further includes a User Interface 150 configured to provide estimates and/or predictions made using Image Analysis Logic 130 to a user. User Interface 150 optionally includes a graphical user interface (and the logic associated therewith) and may be displayed on an instance of Image Generator 110, a mobile device (in which case User Interface 150 can include a mobile app.) or on a computing device remote from Image Generator 110 and/or Image Analysis Logic 130. For example, User Interface 150 may be configured to display at least one or two of: the gestational age of the fetus at birth, the estimate that the fetus will be born prematurely, an estimated time to birth, and/or an estimated gestational age. In some embodiments, User Interface 150 is configured for a remote user to upload one or more ultrasound images for processing by Image Analysis Logic 130.

As is discussed further herein, in some embodiments, User Interface 150 is configured to provide feedback to a user in real-time. For example, User Interface 150 may be used to give instructions to an ultrasound technician during an ultrasound session, so as to generate images which result in a better prediction and/or estimate related to premature birth.

Prediction System 100 optionally further includes a Data Input 160 configured to receive data regarding a pregnancy, e.g., clinical data regarding the fetus and/or a mother of the fetus. Data Input 160 is optionally configured to receive any of the clinical data discussed herein, which may be used by Image Analysis Logic 130 to generate the estimates and/or probabilities discussed herein. For example, this data can include any of the clinical data discussed herein, or inputs from a user of Image Generator 110. In some embodiments, Data Input 160 is configured to receive medical images, such as ultrasound images, from remote sources.

Prediction System 100 optionally further includes Feedback Logic 170. Feedback Logic 170 is configured to guide acquisition of ultrasound images based on a quality of the estimate and/or predictions related to the pregnancy. For example, if analysis of ultrasound images, using Image Analysis Logic 130, obtained during an imaging session results in predictions and/or estimates having inadequate precision, accuracy, and/or reliability, then Feedback Logic 170 may use User Interface 150 to inform a user that additional ultrasound images are desirable.

Further, in some embodiments, feedback logic is configured to direct a user to obtain ultrasound images of specific features such as motion of a fetal heartbeat, fetal heart rate, the placenta, the cervix, fetal blood flow, fetal bone development, fetal spine, fetal kidneys, fetal capillary perfusion, Umbilical Artery, Uterus, Lower Uterine Segment, cervical view taken specifically to measure the length of the cervix, Amniotic Fluid Index (AFI) view, Abdominal Circumference (AC), Biparietal Diameter (BPD) along with any other views of the brain, femur, humerus, endometrium, endometrium vascularization, the edge of the placenta relative to the cervix, the fetal kidneys, the adnexa, and/or the like. In some embodiments, Image Analysis Logic 130 is configured to classify ultrasound images according to subject matter and/or objects included within the images. For example, separate subject matter classes may include any of the views and/or features discussed herein. In such embodiments, Image Analysis Logic 130 may be configured to identify objects in the ultrasound images and determine that there are sufficient quality images of objects in each subject matter classification. (Subject matter classification is not to be confused with classification of ultrasound images according to a class of expected gestational age at birth.) If there are not sufficient images, then the User Interface 150 may be used to request that on operator of Image Generator 110 obtain additional images including the additional objects. Feedback Logic 170, thus, may be configured to indicate a need to acquire additional ultrasound images useful in the estimation that the fetus will be born prematurely. In a specific example, Image Analysis Logic 130 may be configured to request at least one set of images indicative of a gestational age of the placenta and at least one set of images indicative of a gestational age of the fetus (e.g., fetal bone development, and/or fetal heart motion), and optionally one set of images showing the condition of the uterus. In some instances, Feedback Logic 270 is configured to guide a positioning of the image generator (e.g., an ultrasound head) so as to generate images more useful in the estimation that the fetus will be born prematurely. Such guidance may include positioning of an ultrasound probe in a specific position or a written/audio request such as "obtain images showing full femur length."

In various embodiments, Feedback Logic 170 is configured to is configured to guide or request acquisition of new images that would be beneficial to training future models to obtain greater accuracy.

Prediction System 100 optionally further includes Training Logic 180. Training Logic 180 is configured for training Image Analysis Logic 130, Feedback Logic 170, Image Acquisition Logic 190, and/or any other machine learning system discussed herein. Such training is typically directed at the end goal of learning to make quantitative predictions and/or estimates relating to whether a fetus will be born prematurely. For example, Training Logic 180 may be configured to train Image Analysis Logic 130 to make a quantitative prediction and/or estimate of the gestational age of a fetus at birth. As described elsewhere herein, this prediction may be made using both a quantile regression algorithm and a classification algorithm, together or separately.

While Training Logic 180 may use any applicable selections of the commonly known neural network training algorithms, Training Logic 180 optionally includes a variety of improvements to better train the neural networks disclosed herein. For example, in some embodiments Training Logic 180 is configured to pretrain a neural network of Image Analysis Logic 130 to better recognize features in ultrasound images. This pretraining can include training on images with varying orientation, contrast, resolution, point of view, etc., and can be directed at recognizing anatomical features within the ultrasound images. Pretraining is optionally performed using unlabeled data.

In some embodiments, Training Logic 180 is configured to generate additional training images, in cases where training images for a specific condition are sparse or infrequent. For example, once it is known which images and features are most predictive, Training Logic 180 can take subsets of the images, and use a GAN (Generative Adversarial network) to generate new training images including the features that predict extreme premature births or the like.

In some embodiments, Training Logic 180 is configured to train on multiple sets of images, the images optionally being from different mothers. By training on multiple sets of images, rather than on single images overfitting of the data can be reduced. Preferably, each of the sets is large enough to assure that there are at least some images within the set including information useful for making the quantitative predictions discussed herein.

In some embodiments, Training Logic 180 is configured to train Image Analysis Logic 130 to enhance images. For example, Image Analysis Logic 130 may be pretrained to enhance poor quality ultrasound images, or to reveal features, such as fetus capillary perfusion and/or vascularization, that would not normally be visible in the ultrasound images being processed. Such enhancement may allow the use of a handheld ultrasound image to generate the images processed to make quantitative predictions related to preterm birth.

Prediction System 100 optionally further includes Image Acquisition Logic 190. Image Acquisition Logic 190 is configured to acquire the training images and birth information from unusual sources, such social media accounts. For example, Image Acquisition Logic 190 may be configured to scrape social media accounts (i.e., Instagram or Facebook) and automatically identify prenatal ultrasound images and then to correlate those images with birth announcements posted within the same social media accounts. A time between the ultrasound images and birth announcements can be used to approximate a time between acquisition of the ultrasound and the birth, i.e., a gestation time remaining until birth. Such social media acquired information is optionally used by Training Logic 180 to train Image Analysis Logic 130. In some embodiments, ultrasound images (or videos) retrieved from social media will include a date on the image or on the social media website. It is also somewhat common to have a gestational age written on the images.

In some embodiments, Training Logic 180 is configured to train neural networks in multiple stages, e.g., as in transfer learning. For example, a neural network may first be trained to recognize relevant fetus feature, then be trained to estimate gestational age, and then be trained to provide a quantitative estimate of gestational age at birth or length of time to birth.

Prediction System 100 typically further includes a Microprocessor 195 configured to execute some or all of the logic described herein. For example, Microprocessor 195 may be configured to execute parts of Image Analysis Logic 130, Calculation Logic 140, Feedback Logic 170, Training Logic 180, and/or Image Acquisition Logic 190. Microprocessor 195 may include circuits and/or optical components configured to perform these functions.

Figure 2:
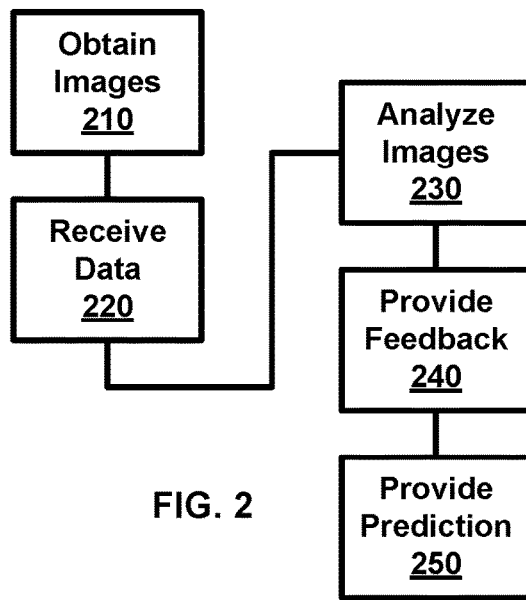
FIG. 2 illustrates methods of making a quantitative prediction, according to various embodiments of the invention.

FIG. 2 illustrates methods of making a quantitative (optionally medical) prediction, according to various embodiments of the invention. A quantitative prediction is optionally used to provide specific corrective treatment in anticipation of a premature birth. As such, the methods of FIG. 2 are optionally followed by appropriate therapy and/or treatment.

In an Obtain Images Step 210, a set of one or more images are obtained. These images are typically related to a specific patient, e.g., an expectant mother and her fetus. These images may be obtained from a source external to Prediction System 100 or may be obtained using Image Generator 110. For example, in some embodiments, ultrasound images are uploaded to Storage 120 via a computer network such as the internet. Images may be received from an electronic medical records system. In other embodiments, images are generated using a medical imaging system such as any of those discussed herein. The images are optionally stored in Storage 120. The images can include any combination of the views and/or features discussed herein and are optionally classified based on their respective views and features (subject matter classification).

In an optional Receive Data Step 220, additional clinical data regarding the patent (mother or fetus) is received. Again, this data may be received from an electronic medical records system, provided by the patient, and/or provided by a caregiver. The received clinical data can include any of the clinical data discussed herein and is optionally received via Data Input 160.

In an Analyze Images Step 230 the images obtained in Obtain Images Step 210 are analyzed using Image Analysis Logic 130. The images are analyzed to produce one or more quantitative predictions. In the case of pregnancy, the quantitative prediction typically includes a quantitative estimate relating to the premature birth of a fetus. For example, the quantitative prediction can include an estimate of a current (at the time the images were recorded) gestational age of the fetus, an estimate of time until birth of the fetus, and/or an estimate of a gestational age of the fetus at birth. The prediction is a "quantitative prediction" as defined elsewhere herein. In addition to the images, the quantitative prediction is optionally further based on the clinical data received in Receive Data Step 220. The methods of analysis in Analyze Images Step 230 can include any combination of the algorithms and/or machine learning systems discussed elsewhere herein, including those discussed with reference to Image Analysis Logic 130. For example, analyzing medical images can include using a quantile regression algorithm and/or a classification algorithm to make a quantitative prediction relating to premature birth of the fetus. In another example, analyzing the medical images includes using a regression algorithm to provide an estimate that the fetus will be born prematurely, and optionally to estimate the time until birth, the regression algorithm being configured to classify an estimated gestational age of the fetus at birth into one of at least two or three time ranges.

Examples of quantitative predictions that may be generated in Analyze Images Step 230 include a probability that the fetus will be born preterm, probabilities that the fetus will be born within one, two or more preterm ranges, a probability that the birth will be induced, probability that the fetus will be born within a future time period (a "future time period" being a time period with a start date in the future), classification of the birth as "borderline preterm," "preterm" or "extreme preterm" (where these classes have defined time periods), a prediction of an adverse medical condition related to the pregnancy, a prediction of post birth health issues for the mother and/or fetus, a prediction that the placenta will not be expelled intact, and/or the like.

In an optional Provide Feedback Step 240, a user (e.g., a caregiver) is provided with feedback regarding acquisition of the images. This feedback can be based on, for example, a quality of the quantitative prediction and/or a classification of images already acquired. In specific examples, during an ultrasound session, a caregiver may be asked to acquire additional images of different resolution, of different views, of different features, and/or the like. Obtain Images Sep 210 and Analyze Images Step 230 are optionally repeated following Provide Feedback Step 240.

In a Provide Prediction Step 250 the quantitative prediction(s) generated in Analyze Images Step 230 is provided to a user, e.g., a patient or caregiver. The predictions are optionally also placed in Storage 120 and/or an electronic medical records (EMR) system. In various embodiments, the predictions are provided via a web interface, via the EMR system, via a mobile application, on a display of Image Generator 110, on a display of a computing device, and/or the like.

FIG. 3 illustrates methods of training a medical prediction system, according to various embodiments of the invention. The methods illustrated by FIG. 3 are optionally used to train Image Analysis Logic 130, Feedback Logic 170, and/or Image Acquisition Logic 190. The methods may be performed using Training Logic 180.

In a Receive Images Step 310, a plurality of medical images are received as a training set. The received medical images optionally include ultrasound images of a fetus during pregnancy. The received images are optionally obtained using the methods illustrated by FIG. 5 and may be stored in Storage 120.

In an optional Classify Step 320, the received images are classified according to the views or features included within the images. For example, an image may be classified as showing the fetal heart or classified as showing the placenta. Classify Step 320 is optionally performed by a neural network included in Image Analysis Logic 130 and/or trained by Training Logic 180. Classify Step 320 may also include classifying images according to (actual or estimated) gestational age of a fetus in each image, and/or a known outcome of their respective pregnancy. For example, images may be classified as having been generated at the 12th week of pregnancy, may be classified as being of a fetus that was born a number of weeks after the image was generated, and/or may be classified as being of a fetus/mother that resulted in a premature birth (of varying degrees of prematurity).

In an optional Filter Step 330, the received images are filtered. The filtering can include removing images that lack features or views that have been determined to have little or no predictive value. For example, a class of images of a mother's bladder may be determined to have little value in determining a quantitative prediction, and this class of images may be removed from the training set. Images may also be filtered according to their quality or resolution, etc.

In some embodiments, Filter Step 330 includes balancing of a number of images in various classes. For example, for training purposes, it may be desirable to have roughly equal numbers of extremely premature births, premature births, induced births, and full-term births. Specifically, balancing may be used to adjust quantities of the images based on gestational age at birth. Likewise, for training purposes, it may be desirable to balance numbers of images within the training set based on classification of views and/or features as determined in Classify Step 320.

In an optional Pretrain Step 340, the neural network is optionally, pretrained to recognize features within the images or types of images. For example, a neural network within Image Analysis Logic 130 may be pretrained to recognize features in ultrasound images of varying orientation, resolution, and/or quality.

In a Train Step 350, the neural network is trained to provide a quantitative prediction regarding birth of the fetus. As discussed elsewhere herein, the quantitative prediction can include an estimate of a gestational age of the fetus at birth, an estimate of a current gestational age of the fetus, and/or an estimate of remaining time until birth of the fetus.

In an optional Test Step 360, predictions may by the neural network trained in Train Step 350 is tested using test images. This testing may be performed to determine the accuracy and/or precision of the quantitative predictions generated by the neural network.

FIG. 4 illustrates methods of identifying a beneficial therapy based on medical predictions, according to various embodiments of the invention. The systems and methods disclosed herein that allow for quantitative predictions of medical conditions and/or outcomes provide new opportunities for identification of beneficial therapies. For example, therapies that could prevent or ameliorate an undesirable medical condition or event. The quantitative nature of the predictions disclosed herein allow for quantitative changes in outcome to be detected and used in evaluation of the efficacy of a therapy. This approach may be used in any of the medical conditions discussed herein. Further, the medical condition need not be present or apparent at a time the quantitative prediction is determined. The therapies may include administration of a pharmaceutical or a physical treatment. In a specific example, the efficacy of a physical treatment including bed rest can be prescribed and/or evaluated for an expectant mother based on ultrasound images obtained at least 1, 2, 3, 4 or 6 months before birth. The therapies may further include follow-up ultrasounds and evaluation.

The quantitative prediction of a future medical condition or event is optionally used to selectively select a population for a clinical trial. For example, assuming that extremely premature births occur in less than 1% of pregnancies, it would be inefficient to give a general population of expectant mothers a candidate therapy in order to detect a benefit to the unidentified 1% early in pregnancy. However, by identifying the 1% of the pregnancies most likely to result in the extremely premature births a study can be made of the benefit seen within this population for a candidate therapy. Such a study is much more efficient and more likely to reveal benefits with better statistical relevance. The systems and methods disclosed herein may be used to identify such preferred populations for clinical studies. This approach is particularly beneficial for conditions that begin development (and could benefit from therapy) well before clear symptoms appear, e.g., Alzheimer's or dementia.

In a Determine Prediction Step 410, a quantitative prediction of a future medical condition is determined for a specific patient. As is discussed elsewhere herein, the quantitative prediction can include a probability that the medical condition will occur within a future time range, and the quantitative prediction can be based on analysis of medical images of the patient. As used herein, a "future" time range is meant to indicate a time range that begins at a time in the future, rather than a time range that begins at a current time. For example, at the time a second trimester ultrasound is obtained a future time range may be 1-2 or 2-4 weeks prior to a full-term pregnancy. The quantitative prediction may be made using any of the systems and/or methods claimed herein. In various embodiments, a time delay between determining the quantitative prediction and the future time range may be weeks, months or years. For example, for premature birth the delay may be at least 1, 2, 3, 4 or 5 months.

In a Provide Candidate Step 420, a candidate therapy is provided to the specific patient. The therapy may include administration of a pharmaceutical and/or a physical treatment such as bedrest, a specific diet, physical exercise, physical therapy, a mental exercise, dialysis, use of supportive clothing, etc. In some embodiments, the candidate therapy is only provided to patients meeting a criterion in their quantitative prediction. Optionally, the candidate therapy is only provided to patents having a quantitative prediction of the medical condition occurring within the future time range of greater than 50%, 66% or 75%. For example, a pharmaceutical may only be provided to expectant mothers having an over 75% risk of extreme premature birth of their fetus. The candidate therapy may be provided to the patient prior to the patient exhibiting any outward symptoms of the medical condition.

In a Repeat Step 430, the steps of determining a quantitative prediction of a future medical condition and providing a candidate therapy is repeated for plurality of patients. The number of patients may be selected so as to include a statistically sufficient population.

In a Determine Relevancy Step 440 it is determined if the candidate therapy resulted in a statistically relevant benefit to the plurality of patients at their respective time ranges. Determine Relevancy Step 440 typically occurs at some time after Determine Prediction Step 410 and Provide Candidate Step 420 for each respective patient. Determine Relevancy Step 440 may be performed for more than one respective time range for each patient and/or different respective time ranges for different patients. The time range(s) being those at which the future medical condition was predicted in Determine Prediction Step 410. Determine Relevancy Step 440 optionally includes comparing patients given the candidate therapy with patients give placebos. As used herein a "statistically relevant benefit" is a benefit that would lead to acceptance and/or governmental approval of the therapy.

In an Identify Step 450, the candidate therapy is identified as the beneficial therapy based on the statistically relevant benefit. Note that an improvement statistically associated with a candidate therapy is also an indication that patients in a population are compliant with an intervention. This information is optionally used to improve interventions (therapies).

FIG. 5 illustrates methods of acquiring ultrasound images, according to various embodiments of the invention. In these methods, postings to social media accounts are used to generate training data, which is optionally used to perform the training methods illustrated in FIG. 3. The methods illustrated in FIG. 5 are optionally performed using Image Acquisition Logic 190 and may be applied to images other than ultrasound images.

In a Scrape Step 510, the contents of social media accounts, such as Facebook® or Instagram® are reviewed and their contents accessed. This access may be performed using a browser or an automated system such as a web crawler.

In an Identify Image Step 520, an ultrasound image, including a fetus, is identified within the accessed social media accounts. The social account name (e.g., a username and/or URL) and posting date of this image is noted. Optionally, but not necessarily, the ultrasound image is downloaded and stored in Storage 120.

In an Identify Birth Step 530, the social media account noted in Identify Image Step 520 is revisited to identify an announcement of a birth. It is then assumed that the birth announcement is associated with the fetus seen in the ultrasound image.

In a Calculate Step 540, a time between posting of the ultrasound image on the social media account and posting of the birth announcement on the social media account is calculated. It is then assumed that the calculated time represents a time between generation of the ultrasound image and the birth.

In a Train Step 550, the ultrasound image and the calculated time use used to train a neural network. The neural network is optionally included within Image Analysis Logic 130 and is trained to generate an optionally quantitative prediction that an ultrasound image is indicative of a premature birth.

The various methods illustrated in FIGS. 2-5 are optionally used in combination and are optionally performed using the systems illustrated by FIG. 1. For example, the methods of FIGS. 2 and 3, and/or 3 and 4 may be used together. The methods of FIG. 5 may be used to generate training data for the other methods disclosed herein.

Example: The Following is an Illustrative Example, which May be Included in any of the Embodiments Discussed Herein All ultrasounds from any gestational ages are used to train the neural networks discussed herein. However, different models can be created for ranges of gestational age.

Note: The following models are simply individual embodiments that show how to create a working model. Many of the hyperparameters such as the learning rate, batch size, and number of epochs can be adjusted without issue.

Import all the libraries used in the code
from fastai2.vision.all import*

Any study where the baby was born before 37 weeks gestational age is classified as "Preterm" in general, 37 weeks or longer is classified as "Normal".

The Preterm category is commonly broken down further into three groups:
Extremely Preterm (less than 28 weeks)
Very Preterm (28 to 32 weeks)
Moderate Preterm (32 to 37 weeks)
However, this particular breakdown is not strictly necessary, other classifications may be used.

The following path is a folder containing one subfolder for each class to be predicted which are "Extremely Preterm", "Very Preterm", "Moderately Preterm", or "Normal". This is only one embodiment, any number of different classifications would also work. For example, there may be two, three, four or more classes.

Preterm births are about 10% of the total in the dataset used, however training may be more effective when using a balanced dataset which is the case here. The validation set is not balanced in this embodiment which reflects the accuracy of the distribution in the real world, but could be balanced in other embodiments. In some embodiments the neural network has an equal chance of being fed an instance of one of the four categories. In various embodiments, at least 50% or 75% of the training set includes images balanced among the possible classes.

Optionally, setting the image size to 400 by 400 pixels. Most of the images in this dataset are several times this size and are reduced in size for training and inference efficiency. Accuracy can increase with increasing image size, however there are diminishing returns. Alternative embodiments use images of at least 224×224; 640×640 pixels or 2048×2048 (pixels), or any range therebetween.

image_size=400

This will create an object to feed data to the neural network during training and validation. 10% of the studies are put into a validation set which is used to monitor training. The validation set contains the same distribution of prematurity that exists in the training data and in the developed world in general. The data is imbalanced for training, however the validation set is the natural distribution and not balanced in any way. The batch size is arbitrarily set to 28 images and can be adjusted if necessary. Adding the function aug_transforms causes each image to be randomly augmented which can reduce overfitting. Examples of augmentation include but are not limited to adjusting brightness, contrast, and flipping the image horizontally. This embodiment uses Binary Cross Entropy as the loss function and it is training as a multi-label classification problem even though there is exactly one label for each image. Other embodiments could use other loss functions such as categorical cross entropy, or mean squared error if the data is viewed as a regression problem.

```
def multi_l(l):
    return [l]
tfms = aug_transforms( )
fnames = get_image_files(path)
dblock = DataBlock(blocks  = (ImageBlock, MultiCategoryBlock),
    get_items = get_image_files,
    get_y    = Pipeline([parent_label, multi_l]),
    splitter = GrandparentSplitter( ),
    item_tfms = Resize(image_size),
    batch_tfms=[*tfms])
dls = dblock.dataloaders(path, bs=48)
```

Create an object which will control training and inference at a high level. Using a high value for weight decay is one embodiment. Other forms of regularization of the weight values may have similar effect.

Obtain a pretrained network for use in transfer learning, however training a neural network from an initial randomized form will also work. In this case ResNet-152 is used. Other variations of resnet will work and the more layers the better the accuracy. Many other neural networks will also give usable results. The example below illustrates an example of training. The parameters and steps may be varied in alternative embodiments.

```
learn = cnn_learner(dls,
    resnet152,
    cbs=[ShowGraphCallback( )],
```

-continued

```
    wd=0.1,
    metrics=[partial(accuracy_multi, thresh=0.5)],
    loss_func=BCEWithLogitsLossFlat( ))
```

This will freeze the parameters of the convolutional part of the neural network and will allow training of the just the linear layers. Other embodiments will not necessarily require the step of freezing layers.

learn.freeze( )

Train the neural network for 10 epochs while gradually increasing then decreasing the learning rate with a scheduler. The maximum learning rate will be 1e−3. Other embodiments may use an alternative training schedule.

learn.fit_one_cycle(10, 1e−3)

This will allow the entire neural network to be trained including the convolutional layers.

learn.unfreeze( )

Further train the neural network for 5 epochs while gradually increasing then decreasing the learning rate with a scheduler. The maximum learning rate will be 1e−5.

learn.fit_one_cycle(5, 1e−5)

Further train the neural network for 5 epochs while gradually increasing then decreasing the learning rate with a scheduler. The maximum learning rate will be 1e−5.

learn.fit_one_cycle(5, 1e−5)

Best validation accuracy of this embodiment is 86%, if the threshold for prediction is set at 0.5.

This network allows for the determination of which specific anatomical views of the study are most useful for making this prediction. Specific anatomical views or any other information fed to the network can be excluded if it is commonly uninformative, or the various views can be weighted in calculating the final prediction.

Each prediction outputs a score of how confident the model is which can be used in real time on the ultrasound machine to inform the ultrasound technician when a view which will improve accuracy is obtained, or the software can automatically capture high confidence views as they are found with no effort from the technician required. This technique can be used to create training sets for continuous improvements in updated models which is a feedback loop to capturing better data for training future models.

The trained system is optionally used to provide an ultrasound technician real-time feedback. For example, the system may inform the technician when images expected to be the most predictive have or have not been obtained. The system can request that the technician obtain images of specific anatomy of the mother, fetus, or both. When an obtained image is identified as being predictive of a premature birth, the system may request that the technician obtain additional to confirm or negate the prediction of premature birth. For example, if an image of one part of fetal anatomy (e.g., a heart) predicts a premature birth the system may request that the technician obtain further images of that anatomy or further images of another part of the embryo's anatomy (e.g., hands or face).

It was determined that making predictions based individual ultrasounds and then naively aggregating these individual predictions was useful, but can be improved upon. The biggest problem with this method is that within a single ultrasound recording session some ultrasound images may show a confident preterm prediction while ultrasound images of other part of the anatomy will confidently predict a normal outcome making a simple aggregation less effective. This led to the decision to create neural networks allowing multiple images to be classified in a single pass through a neural network or sequence of networks. As the number of images simultaneously fed into a neural network increased the accuracy also typically increased. Therefore, more efficient methods of passing (in parallel, or sequentially) multiple images through a single network (or sequence of networks) were developed.

This does not necessarily have to be a classification problem. The values to predict could be numeric values representing the desired target and a neural network to perform a regression is created instead.

Training data can be created by training a neural network to modify images from one class into another if the data is limited for a particular class. An example of a neural network which can convert images from one class to another is a cyclegan.

It is not necessary for images to be used. The underlying sound waves captured by the ultrasound machine before conversion into an image could also be used as an alternative to or in addition to images for this prediction.

CNN-LSTM (Convolutional Neural Network—Long Short-Term Memory)

It was then determined that a neural network could be created which could extract the useful information from each image which is then aggregated using multiple neural networks combined into a single neural network, however these networks could be separate in another embodiment. An ultrasound session is one in which a technician takes a set of images in one interaction with a patient. Considering many ultrasound sessions exceed 100 images this is useful for processing efficiency and accuracy. LSTMs are designed to be used with sequential (or time series) data where data points are correlated in a sequence. The ultrasound images in an ultrasound session don't have a significant amount of order to them, if any, however this type of network will carry information from a previous step of processing a single image forward and this combined information can be classified after each image in an ultrasound session is processed. Ultrasound sessions do not have a significant amount of order because an ultrasound technician typically jumps from viewing one anatomical feature to another anatomical feature. It should be noted that the anatomical features used do not have to be exclusive to the mother or the fetus, but may be a combination of both. It is possible to record a video of the entire session and in that embodiment the images in the video would have a sequential nature and this general technique could be employed.

```
from fastai2.vision.all import *
from pathlib import Path
```

Get the data which is divided into training, validation, and test sets. The training data is created in an unusual way. Instead of just using each study as a separate folder of images, folders are created which randomly sample a range of images from pools of all normal studies and all preterm studies. It is also possible to sample images from a pool of each class of the desired sequence length at run time. Other embodiments could use 2, 3 or more classes or numeric values. There are a few reasons to do this.

First, the gestational age of many ultrasound sessions has an error range that overlaps the 37-week boundary, which means the training data would contain a significant number of mislabeled studies.

Second, some preterm studies are done before the cause of the preterm birth has presented itself, or the cause of the preterm birth is not visible in an ultrasound at any point in time.

By taking a random selection it makes it possible for each training sample to have some ultrasounds which contain the needed information to make a correct prediction.

An alternative method for prediction is to predict the time until birth from the date of the ultrasound and then calculate which class that time frame would fall into. This prediction is also useful without making a subsequent classification.

It should also be noted that multiple ultrasound sessions are commonly performed on a single pregnancy. Multiple sessions from a single pregnancy could also be combined when performing a prediction.

A single session may indicate an impending preterm birth but may not have a high confidence. Therefore, the system may indicate that a follow up session is desired and potentially when the follow up session should be conducted.

It is generally believed that preterm birth may have multiple underlying causes which would suggest different treatments. The network can inform the physician of which anatomical views are the cause of a preterm prediction allowing more informed treatment options.

The errors in prediction made by the neural network can be used to determine new treatments for or greater understanding of preterm birth. For example, if the network predicted a preterm birth, yet the child was not born preterm, the medical data of the patient can be data mined for commonalities which would allow for the discovery of new treatments.

Data Acquisition

Get paths to each folder containing the images from a single study

```
def get_sequence_paths(path):
    sequence_paths = [ ]
    for folder in path.ls( ):
        for c in folder.ls( ):
            sequence_paths += c.ls( )
    return sequence_paths
folders = get_sequence_paths(IMAGES_PATH)
```

The length of sequences is 36 images in this example, but a smaller or larger range can be used. More images is likely to work better but with diminishing returns. The image size being used is 400×400 pixels which is significantly larger than the 224×224 pixels typically used for image classification problems. However, both smaller and larger images will also work.

```
seq_len = 36
image_size = 400
class ImageTuple(Tuple):
    def show(self, ctx=None, **kwargs):
        n = len(self)
        img0, img1, img2 = self[0], self[n//2], self[n-2]
        if not isinstance(img1, Tensor):
            t0, t1, t2 = tensor(img0), tensor(img1), tensor(img2)
            t0, t1, t2 = t0.permute(2,0,1), t1.permute(2,0,1), t2.permute(2,0,1)
        else: t0, t1, t2 = img0, img1, img2
        return show_image(torch.cat([t0, t1, t2], dim=2), ctx=ctx, **kwargs)
```

-continued

```
class ImageTupleTransform(Transform):
    def __init__(self, seq_len=36):
        self.seq_len = seq_len
    def encodes(self, path):
        images = path.ls( )
        return ImageTuple(tuple(PILImage.create(f) for f in
L(random.choices(list(images), k=self.seq_len)) if os.path.isfile(f)))
tfms = aug_transforms(flip_vert=False)
grandparent_splitter = GrandparentSplitter( )(files)
itfm = ImageTupleTransform(seq_len=seq_len)
ds = Datasets(files, tfms=[[itfm], [parent_label, Categorize]],
splits=grandparent_splitter)
dls = ds.dataloaders(bs=bs,
            after_item=[Resize(image_size),
                ToTensor],
            after_batch=[*tfms,
                IntToFloatTensor],
            drop_last=True)
```

The Encoder class takes a model pretrained on single ultrasound images. It removes the final classification layer and returns 512 features for each image. However, in other embodiments the number of features can be as little as one or much greater than 512.

```
class Encoder(Module):
    def __init__(self, **kwargs):
        model = load_learner("resnet152_base_model").model
        self.body = model[0]
        self.head = model[1][:-4]
    def forward(self, x):
        return self.head(self.body(x))
```

The CNNLSTM module takes the features from each image and classifies the entire sequence of images.

```
class CNNLSTM(Module):
    def __init__(self, num_classes=2, lstm_layers=1, hidden_dim=128,
attention=True):
        model = Encoder( )
        nf = 512
        self.encoder = model
        self.lstm = LSTM(nf, hidden_dim, lstm_layers)
        self.head = nn.Sequential(
            LinBnDrop(hidden_dim, hidden_dim, p=0.2, act=nn.ReLU( )),
            nn.Linear(hidden_dim, num_classes),
        )
        self.attention = attention
        self.attention_layer = nn.Linear(hidden_dim, 1)
    def forward(self, x):
        x = torch.stack(x, dim=1)
        batch_size, seq_length, c, h, w = x.shape
        x = x.view(batch_size * seq_length, c, h, w)
        x = self.encoder(x)
        x = x.view(batch_size, seq_length, -1)
        x = self.lstm(x)
        if self.attention:
            attention_w = F.softmax(self.attention_layer(x).squeeze(-1), dim =-1)
            x = torch.sum(attention_w.unsqueeze(-1) * x, dim=1)
        else:
            x = x[:, -1]
        return self.head(x)
    def reset(self): self.lstm.reset( )
model = CNNLSTM(num_classes=dls.c, lstm_layers=1, hidden_dim=128,
attention=True)
```

Create a Learner object which will control training and inference at a high level. Using a high value for weight decay is helpful in making a correct prediction.

GradientAccumulation can be used if GPU memory constraints require it. This will accumulate gradients for 32 items before making an update to the weights of the network.

ModelReseter resets the hidden state of the LSTM between batches.

cnnlstm_splitter allows part of the entire network to be frozen while updating the weights of another part.

```
def cnnlstm_splitter(model):
    return [params(model.encoder), params(model.lstm) +
params(model.attention_layer) + params(model.head)]
learn = Learner(dls,
        model,
        wd=0.3,
        metrics=[accuracy],
        cbs=[ModelReseter( ), ShowGraphCallback( ),
GradientAccumulation( ), SaveModelCallback(monitor='valid_loss',
fname='CNN_LSTM')],
        splitter=cnnlstm_splitter).to_fp16( )
```

Train the neural network for 5 epochs while gradually increasing then decreasing the learning rate with a scheduler. The maximum learning rate will be 1e−3. These parameters are simply chosen for this embodiment, many other choices would also work.

```
learn. freeze( )
learn.fit_one_cycle(5, 1e-3)
```

Alternative Embodiments

To aggregate the individual predictions for a study run each through a tournament to determine final classification.

Reinforcement learning can be used in place of the CNN-LSTM shown.

Use multiple models trained on different subsets of the data to create ensembles which typically increases accuracy.

Use a ConvLSTM which incorporates the CNN model into the LSTM cells in place of the CNN-LSTM shown.

Use additional data about the patient in combination with the images such as age or relevant events in the medical history of a patient.

Additional outputs in addition to the preterm class can be used. Some examples are days until birth, weight at birth, current gestational age among others. Having multiple outputs for prediction can improve the overall accuracy of the prediction due to the inherent relationships between the various items being predicted. Any of these alternative predictions can be performed without the preterm prediction if desired.

CONCLUSION

The systems and methods disclosed herein have been applied to real world data obtained from a clinical context and have been shown to consistently produce a positive predictive value above 90% and a negative predictive value above 90%. In some cases, results including a positive predictive value above 99% and a negative predictive value above 97% have been achieved.

Several embodiments are specifically illustrated and/or described herein. However, it will be appreciated that modifications and variations are covered by the above teachings and within the scope of the appended claims without departing from the spirit and intended scope thereof. For example, while ultrasound images and premature birth are taught herein by way of example, the systems and methods described herein may be applied to other medical information and conditions. Examples, include prediction of Alzheimer's, dementia, multiple sclerosis, long term after-effects of infection, cervical cancer, ovarian cancer, uterine cancer, and/or any other medical condition the precursors of which may be present in an ultrasound image. The methods and systems disclosed may be used to determine a current clinical state separately or in combination with the (optionally quantitative) prediction of a future state. The systems and methods disclosed herein may also be used to predict future health conditions of a fetus after birth. For example, future learning disabilities, cognitive abilities, personality, poor development or function of various organs, and/or the like.

While the teachings herein include use of medical images, e.g., ultrasound images, in various embodiments, the systems and methods may use raw data other than in the form of images. For example, Image Analysis Logic 130 is optionally trained to process raw ultrasound data rather than or in addition to images generated from such data.

The embodiments discussed herein are illustrative of the present invention. As these embodiments of the present invention are described with reference to illustrations, various modifications or adaptations of the methods and or specific structures described may become apparent to those skilled in the art. All such modifications, adaptations, or variations that rely upon the teachings of the present invention, and through which these teachings have advanced the art, are considered to be within the spirit and scope of the present invention. Hence, these descriptions and drawings should not be considered in a limiting sense, as it is understood that the present invention is in no way limited to only the embodiments illustrated.

The "logic" discussed herein is explicitly defined to include hardware, firmware or software stored on a non-transient computer readable medium, or any combinations thereof. This logic may be implemented in an electronic and/or digital device to produce a special purpose computing system. Any of the systems discussed herein optionally include a microprocessor, including electronic and/or optical circuits, configured to execute any combination of the logic discussed herein. The methods discussed herein optionally include execution of the logic by said microprocessor.

Computing systems and/or logic referred to herein can comprise an integrated circuit, a microprocessor, a personal computer, a server, a distributed computing system, a communication device, a network device, or the like, and various combinations of the same. A computing system or logic may also comprise volatile and/or non-volatile memory such as random-access memory (RAM), dynamic random access memory (DRAM), static random access memory (SRAM), magnetic media, optical media, nano-media, a hard drive, a compact disk, a digital versatile disc (DVD), optical circuits, and/or other devices configured for storing analog or digital information, such as in a database. A computer-readable medium, as used herein, expressly excludes paper. Computer-implemented steps of the methods noted herein can comprise a set of instructions stored on a computer readable medium that when executed cause the computing system to perform the steps. A computing system programmed to perform particular functions pursuant to instructions from program software is a special purpose computing system for performing those particular functions. Data that is manipulated by a special purpose computing system while performing those particular functions is at least electronically saved in buffers of the computing system, physically changing the special purpose computing system from one state to the next with each change to the stored data.

What is claimed is:

1. A medical prediction system configured to predict premature births, the medical prediction system comprising:
    an image storage configured to store ultrasound images, the ultrasound images including a fetus;
    image analysis logic configured to provide a quantitative prediction that the fetus will be born prematurely based on the ultrasound images, wherein the image analysis logic is configured to use a regression algorithm to provide the quantitative prediction, including an estimate that the fetus will be born prematurely within a time range and wherein the image analysis logic further comprises
    first logic configured to estimate a gestational age of the fetus based on the ultrasound images, the gestational age being at a time the ultrasound images were generated,
    second logic configured to estimate a time until birth of the fetus based on the ultrasound images, and
    third logic configured to calculate an estimated gestational age of the fetus at birth;
    a user interface configured to provide at least the prediction that the fetus will be born prematurely to a user; and
    a microprocessor configured to execute at least a part of the image analysis logic.

2. The medical prediction system of claim 1, further comprising an image generator configured to generate the ultrasound images.

3. The medical prediction system of claim 2, wherein the image generator comprises a sound source, a sound detector and logic configured to generate the ultrasound images based on sound detected by the sound detector.

4. The medical prediction system of claim 2, wherein the image generator is configured to adapt the generation of the ultrasound images based on an output of the image analysis logic.

5. The medical prediction system of claim 2, wherein the image generator is configured to generate a sequence of images representative of motion of a fetus, the image sequence optionally including fetal blood flow, capillary profusion, and/or heart movement.

6. The medical prediction system of claim 2, wherein the image generator is configured to direct a user to modify a position of a sound source configured to generate the ultrasound images.

7. The medical prediction system of claim 1, further comprising a data input configured to receive clinical data regarding the fetus or a mother of the fetus, wherein an estimated time until birth of the fetus is based on the clinical data.

8. The medical prediction system of claim 7, wherein the image analysis logic is further configured to predict that the fetus will be born prematurely based on clinical data received via the data input.

9. The medical prediction system of claim 8, wherein the clinical data includes at least one of: mother genetics, mother weight, mother pregnancy history, mother blood glucose, mother heart function, mother kidney function, mother blood pressure, placenta condition, mother infections, mother nutrition, mother drug use, mother age, mother cervix or uterus characteristics.

10. The medical prediction system of claim 1, further comprising feedback logic configured to guide acquisition of the ultrasound images based on a quality of the prediction that the fetus will be born prematurely or classification of the images acquired into subject matter classes.

11. The medical prediction system of claim 10, wherein the feedback logic is configured to guide a positioning of the image generator so as to generate images more useful in the prediction that the fetus will be born prematurely.

12. The medical prediction system of claim 10, wherein the feedback logic is configured to indicate a need to acquire additional ultrasound images useful in the prediction that the fetus will be born prematurely.

13. The medical prediction system of claim 1, further comprising training logic configured to train the logic configured to estimate a time until birth of the fetus.

14. The medical prediction system of claim 13, wherein the image analysis logic includes a machine learning system and the training logic is configured to pretrain the machine learning logic to recognize features in the ultrasound images.

15. The medical prediction system of claim 13, wherein the image analysis logic includes a machine learning system and the training logic is configured to train the machine learning system to make the quantitative prediction that the fetus will be born prematurely.

16. The medical prediction system of claim 1, wherein the ultrasound images including the fetus are generated over a period of time including at least three months.

17. The medical prediction system of claim 1, wherein the ultrasound images include doppler information, or fluid, bone or tissue density information.

18. The medical prediction system of claim 1, wherein the image analysis logic is configured to use a regression algorithm to output a range prediction to provide an estimate that the fetus will be born prematurely.

19. The medical prediction system of claim 1, wherein the image analysis logic is configured to provide an estimate that the fetus will be born prematurely using a classification algorithm, the classification algorithm including at least two classifications of birth timing.

20. The medical prediction system of claim 1, wherein the image analysis logic includes a neural network configured to receive the ultrasound images and to generate an output representative of the prediction that the fetus will be born prematurely.

21. The medical prediction system of claim 1, wherein the image analysis logic includes a neural network configured to receive the ultrasound images and to generate an output indicative of a time until birth of the fetus.

22. The medical prediction system of claim 1, wherein the quantitative prediction that the fetus will be born prematurely includes an estimate of a probability that the fetus will be born prematurely, the estimate being based on an ultrasound image, of the ultrasound images, of a cervix and/or amniotic fluid index.

23. The medical prediction system of claim 1, wherein the quantitative prediction is based on an ultrasound image, of the ultrasound images, including an endometrium and/or a uterine wall.

24. The medical prediction system of claim 1, wherein the user interface is configured to provide at least two of: the gestational age, the estimated time until birth and the gestational age of the fetus at birth.

25. The medical prediction system of claim 1, wherein the image analysis logic includes a machine learning system and the training logic is configured to train the machine learning system to use both a regression algorithm and a classification algorithm to make the prediction that the fetus will be born prematurely.

* * * * *